United States Patent [19]
van den Engh et al.

[11] Patent Number: 5,150,313
[45] Date of Patent: Sep. 22, 1992

[54] PARALLEL PULSE PROCESSING AND DATA ACQUISITION FOR HIGH SPEED, LOW ERROR FLOW CYTOMETRY

[75] Inventors: Gerrit J. van den Engh; Willem Stokdijk, both of Livermore, Calif.

[73] Assignee: Regents of the University of California, Oakland, Calif.

[21] Appl. No.: 508,226

[22] Filed: Apr. 12, 1990

[51] Int. Cl.$^5$ .......................... G01R 29/02; H03K 5/19
[52] U.S. Cl. ..................................... 364/569; 364/486; 364/550; 395/550; 395/725; 395/800
[58] Field of Search ............... 364/486, 569, 555, 178, 364/179, 200, 900, 550; 395/250, 275, 550, 725, 800

[56] References Cited

U.S. PATENT DOCUMENTS

| | | | |
|---|---|---|---|
| 3,344,406 | 9/1967 | Vinal | 395/425 |
| 4,525,673 | 6/1985 | Berkowitz | 364/900 X |
| 4,669,060 | 5/1987 | Therond et al. | 364/900 |
| 4,748,573 | 5/1988 | Sarandrea et al. | 364/900 X |
| 4,764,687 | 8/1988 | Hamilton et al. | 364/569 X |
| 4,907,229 | 3/1990 | Edwards et al. | 364/200 X |
| 4,943,926 | 7/1990 | Guzman-Edery | 364/486 |
| 4,987,539 | 1/1991 | Moore et al. | 364/555 X |
| 5,010,560 | 4/1991 | Janney et al. | 364/569 X |

Primary Examiner—Parshotam S. Lall
Assistant Examiner—Thomas S. Auchterlonie
Attorney, Agent, or Firm—Henry P. Sartorio

[57] ABSTRACT

A digitally synchronized parallel pulse processing and data acquisition system for a flow cytometer has multiple parallel input channels with independent pulse digitization and FIFO storage buffer. A trigger circuit controls the pulse digitization on all channels. After an event has been stored in each FIFO, a bus controller moves the oldest entry from each FIFO buffer onto a common data bus. The trigger circuit generates an ID number for each FIFO entry, which is checked by an error detection circuit. The system has high speed and low error rate.

25 Claims, 10 Drawing Sheets

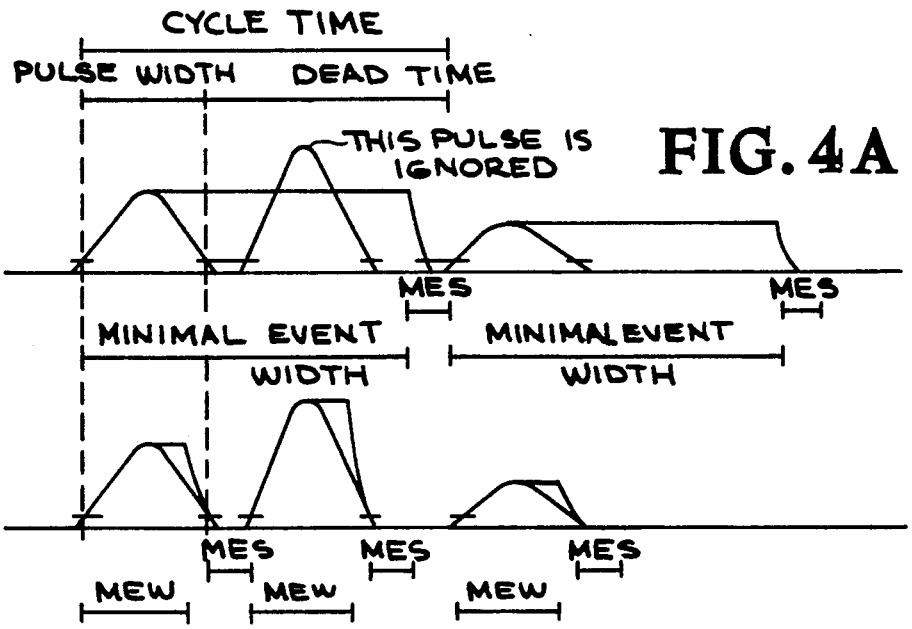
FIG. 4A
FIG. 4B
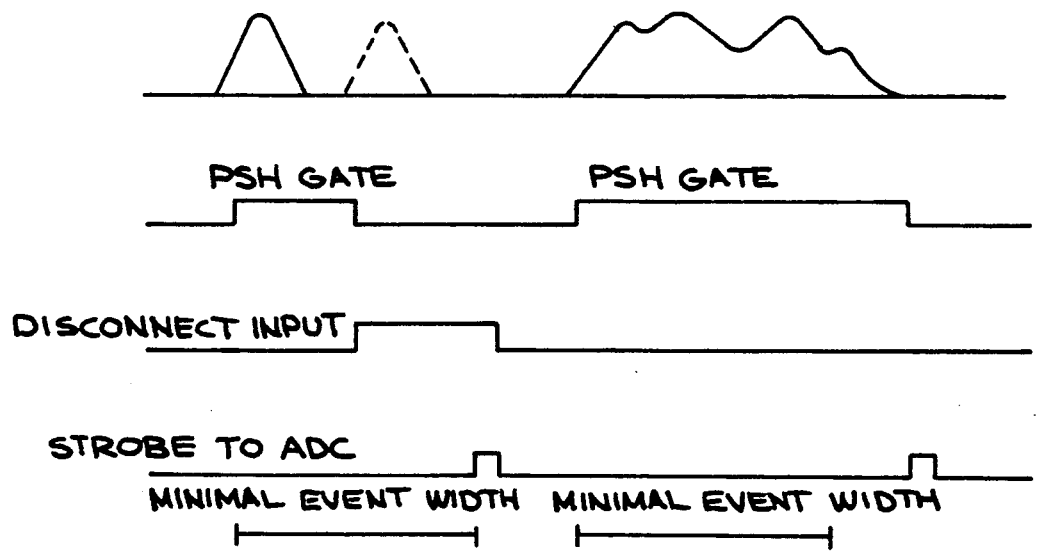
FIG. 7

PARALLEL PULSE PROCESSING AND DATA ACQUISITION FOR HIGH SPEED, LOW ERROR FLOW CYTOMETRY

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates generally to method and apparatus for flow cytometry, and, more particularly, to signal processing and data acquisition for multichannel (including multibeam) flow cytometers.

Flow cytometry is a powerful tool for biological analysis. In a flow cytometer a stream of particles (e.g., cells or cell fragments) which have been chemically tagged, i.e., with a fluorescent dye, flows through an illumination (laser) beam which causes the chemical tag to fluoresce. The light pulses (scatter and fluorescence) provide an identifying signature of the particle. A multilaser flow cytometer uses a plurality of spaced beams each of a different wavelength to excite different fluorescent dyes. Thus more information can be obtained using a multilaser flow cytometer since each cell can be probed successively by each beam to provide information relating to a multitude of characteristics. However, data collection in multibeam systems is operationally more complex because of the time separation between the beams and the uncertain correlation between signals from each beam. Similarly, multiple detectors can be used with each beam, creating similar multichannel data collection problems.

If the signals are obtained with multiple excitation beams, the pulses from a single particle will reach different detectors at different times. The asynchronous events can be correlated either before or after the pulse digitization. One prior art approach to pre-processing synchronization is to hold the pulse values in analog circuits until all measurements of an event have been completed (FIG. 1A). After the event leaves the last measurement beam, the held values are input to AD converters. As shown, the height from the pulse from the first measurement (beam 1) is held until the particle has passed the second illumination point (beam 2). Both pulse heights are then converted into a digitized value, either by a single multiplexed ADC or by two converters working in parallel. The time of measurement cycle (cycle time) is the beam separation time plus the AD conversion time. This has the disadvantage that an event occupies the acquisition electronics for the time it takes to traverse all excitation beams. Thus, in a multilaser flow cytometer, parameter synchronization by sample hold circuits greatly reduces the maximum throughput rate of the system. It is more efficient to delay the earliest pulses with analog delay lines such that all signals enter the acquisition channels simultaneously (FIG. 1B). As shown, the signal from the first beam is delayed with an analog delay line so the signals from the two beams arrive simultaneously at the pulse processing electronics The cycle time is the AD conversion time plus the pulse width. However, analog delay lines have some drawbacks. They are expensive. They may induce signal distortion. They become unmanageable for large numbers of detectors or long delay times.

Flow cytometrists increasingly conceive of meaningful experiments that require multiple illumination beams with several detectors per light source. They demand high sort and analysis rates. At the same time, they expect instruments to accurately identify particles that occur at very low frequencies. A few examples of such experiments are: drug uptake by individual cell populations in complex cell mixtures, chromosome sorting and analysis, and the detection of aberrant cells in a large population of normal cells. Such applications require data acquisition systems with multiple input channels and precisely defined timing protocols. The electronics must be fast and accurate.

SUMMARY OF THE INVENTION

Accordingly, it is an object of the invention to provide pulse processing and data acquisition method and apparatus for a high speed multilaser or multichannel flow cytometer.

It is also an object of the invention to provide pulse processing and data acquisition method and apparatus for a high speed multilaser or multichannel flow cytometer with low error rate.

It is another object of the invention to provide in a multibeam or multichannel flow cytometer method and apparatus for signal processing using a parallel architecture.

It is a further object of the invention to provide an improved correlation between events including coherence and synchronization in a multichannel pulse processing system.

It is another object of the invention to provide signal processing method and apparatus for multibeam flow cytometry which is limited by event pulsewidth rather than beam separation time delay.

The invention is a digitally synchronized, parallel pulse processing and data acquisition system for a flow cytometer/cell sorter including parallel input channels, digitization circuitry on each channel, triggering and timing circuitry, error detection circuitry, data transfer bus, and circuitry for event classification and sorting. The parallel processing system can be built using relatively simple electronic components. The resulting system has virtually no dead time and can be used to analyze and sort particles at a very high rate. Despite the high speed of the system, its error rate can be kept well below that of analog synchronization schemes.

Parallel pulse processing is achieved by equipping each input channel with a set of pulse processing electronics. The detector pulses are immediately converted into digital values which are temporarily stored in first in, first out (FIFO) buffers which are connected to a digital data bus. Digital timing circuitry keeps track of the stored values. After a particle has traversed all illumination beams its measured values are transferred as a package to the acquisition computer over the data bus. The cycle time is determined by the length of the AD conversion process alone. Since the channel has processed the input signals independently, the scheme can easily be extended to any number of input channels and illumination beams.

The flow of data through the parallel input channels is regulated by control circuits. These circuits control the timing of the pulse conversions and keep the data in the FIFO buffers properly correlated. A trigger circuit detects an event at the first measurement beam and activates a control circuit that regulates the data conversion on the other input channels. The trigger circuit keeps the parallel data conversion processes synchronized. The output of the trigger circuit is defined by a minimum pulse width, a minimum event width, and a minimum event separation. The minimum pulse width assures that the trigger circuit puts out a clear signal, even when activated by very short input pulses (glitches). The minimum event width defines the shortest time interval between trigger pulses. This time is determined by the execution time of the longest step in the pulse digitization process. The minimum event width should be slightly longer than the time of the longest step in the pulse digitization process. The minimum event separation prevents closely spaced events from merging into a single trigger pulse. The trigger circuit also assigns an ID number to each pulse. The ID number is attached to all pulses. An error detection circuit can assure synchronization by checking the ID numbers within an event parameter set.

BRIEF DESCRIPTION OF THE DRAWINGS

FIGS. 4A, B illustrate the dependence of the dead time of a parallel processing acquisition system on the cycle time and event width.

FIG. 7 is a timing diagram of the pulse sample hold circuit.

DETAILED DESCRIPTION OF THE PREFERRED EMBODIMENTS

Figure 1A:
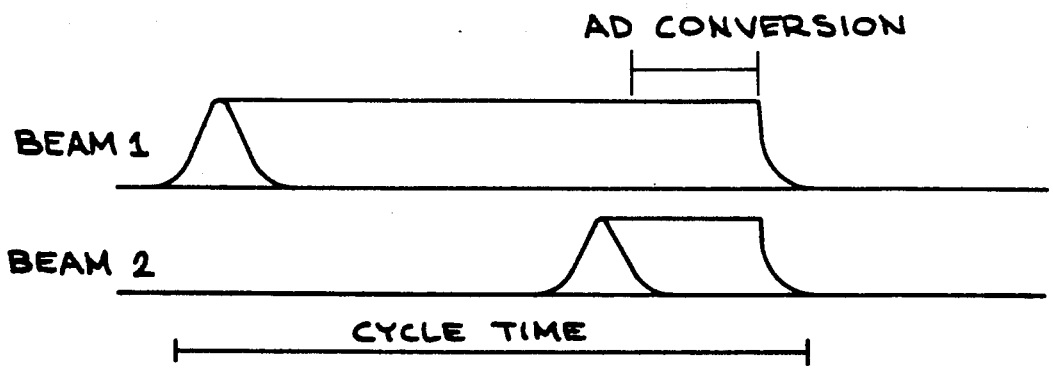
FIGS. 1A–C illustrate three different methods for digitizing pulses from a two-beam flow cytometer, two prior art methods and the method according to the invention, respectively.
Figure 1B:
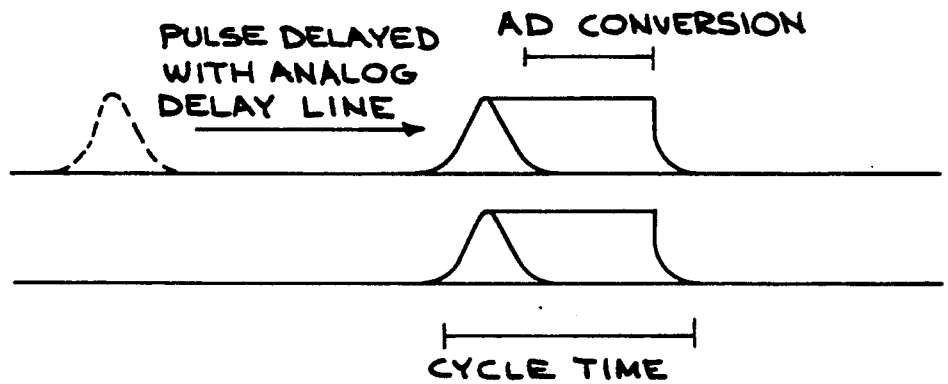

The data acquisition system of the invention for a multilaser or multichannel flow cytometer differs from most instruments in that the signals from a large number of detectors are processed in parallel. The invention applies to multibeam cytometers and also to multiple detectors (multichannels) per beam. Each of the input channels is capable of autonomously measuring and digitizing the fluorescence signals from the particles. The digitized values that belong to one particle are collected by digital circuitry and are presented as a compact data package on a special bus. In addition to the pulse values, the data package contains a time marker, information needed for sort decisions and an error detection code. Electronic modules that read the information from the bus can make complex multiparameter sort decisions at a very high speed. All events can also be recorded as data lists by a computer. The lists can be used to reconstruct a sort or analysis run. The raw data lists can also be reduced to kinetic curves and/or (gated) multivariate histograms.

As a result of the applied scheme of parallel pulse processing, the dead time of the system is independent of the number of parameters measured and the number and time separation of the excitation beams. The cycle time is limited by the AD conversion time. The illustrative instrument embodiment has a cycle time of 5 $\mu$s, which corresponds to a throughput rate of $2 \times 10^5$ events/s. At this rate, the incidence of correlation errors is well below 1 in $10^8$ analyzed particles. The system is reliable and convenient to use in a variety of experiments. Its high speed and low error rate make it well suited for high resolution measurements, rare event analysis, kinetic measurements and high speed cell sorting.

In a multiparameter flow cytometer, the incoming signals are handled most efficiently if each detector is equipped with its own electronics for pulse conditioning and analog-to-digital (AD) conversion. The input channels can then operate in parallel, and all signals can be processed simultaneously. Immediately after completion of the AD conversion, the input channels are ready for the next pulse and do not have to wait for each other before they can proceed. Since all light pulses from a given particle do not necessarily occur simultaneously, parallel pulse digitization requires circuitry that keeps track of the events and that gathers together the values that belong to each particle. Once the values have been properly correlated, they can be presented via a data bus to the computer that stores the data and to the units that make sort decisions.

An acquisition system with buffered parallel input channels that merge onto a common data bus offers great advantages for cell sorting. Despite the random, asynchronous nature of the incoming pulses, the data can be sent via the bus in well-defined, synchronized packages. Event classification and sorting can be done by circuits that read those packages from the bus. Since the sorting is done by dedicated hardware, it can proceed at very high speed. The classification and sort process itself can be divided into parallel operations that can be carried out by parallel modules. The communication between these modules can also take place via the bus. Thus, the bus contains all the information concerning the pulse measurements and the sort decisions. By monitoring the data on the bus, proper operation of the system can be verified. Since all data on the bus can be stored as data lists in a computer, complete experiments can be reconstructed and evaluated at a later date.

Correlating Signals from Different Excitation Beams

Figure 1C:
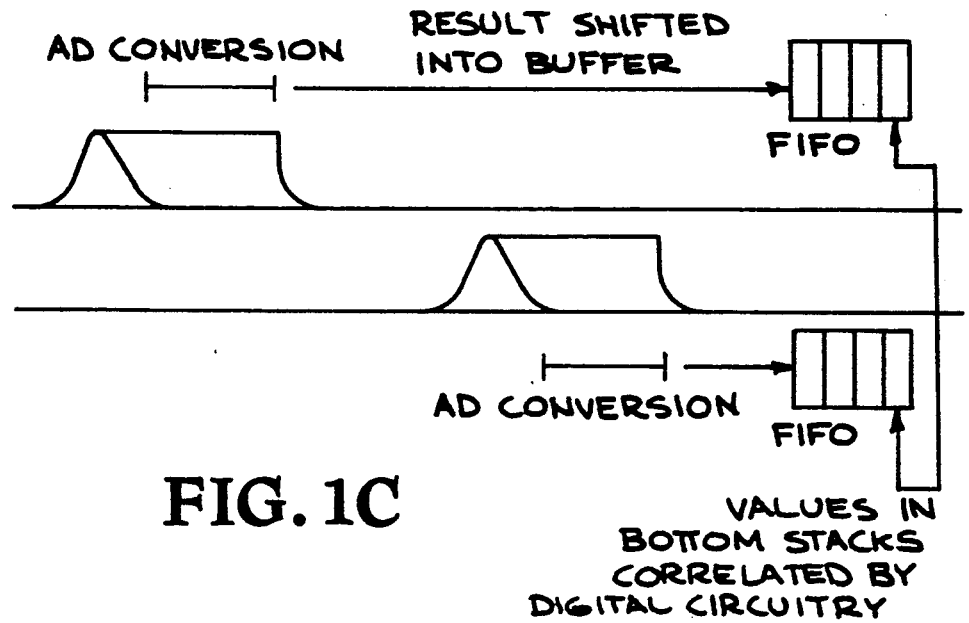
Figure 2A:
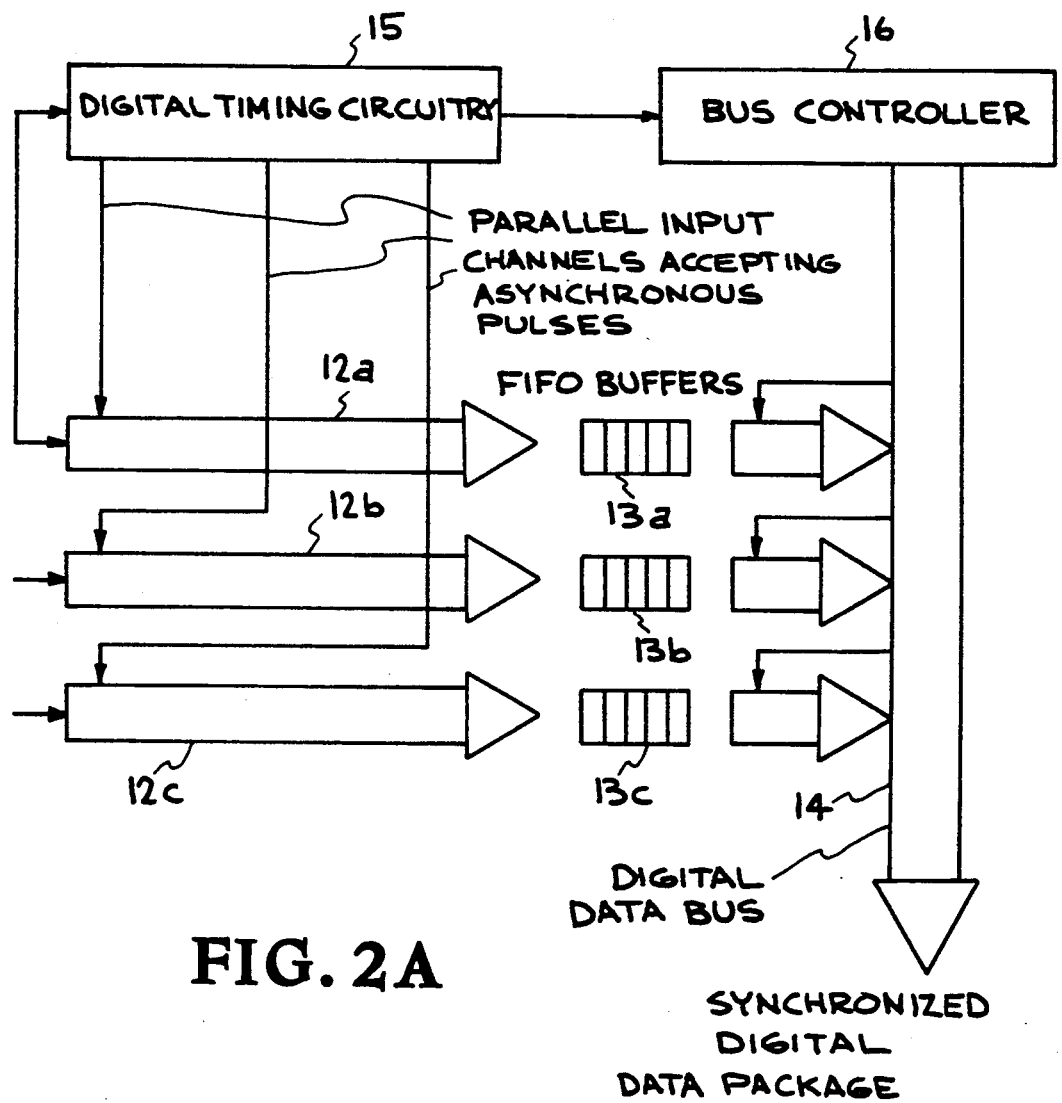
FIG. 2A is a schematic diagram of parallel, pulse processing, input channels connected through FIFO buffers to a common digital bus.

According to the invention, in acquisition systems for flow cytometers with multiple excitation beams or systems that are used to measure a large number of parameters, it is best to correlate the parameter values after pulse digitization. In such a scheme, the pulses are converted into digital values as soon as they are registered by the detectors. Each channel has pulse processing circuitry. These values are temporarily stored in first-in-first-out (FIFO) buffers, (FIG. 1C). The values stored in the FIFO buffers are correlated by digital circuitry. After an event has been seen by all the input channels, the stored values are combined and transferred over a bus to the acquisition computer. As shown in FIG. 2A, parallel pulse processing input channels 12a,b,c are connected through FIFO buffers 13a,b,c to a common digital bus 14. Digital timing circuitry 15 controls the pulse sampling and AD conversion by the input channels. A bus controller 16 collects the results of the pulse conversion process and transfers the data that belong to the same event in a compact package over the data bus.

The correlation of digitized data offers advantages over the synchronization of analog signals. A digital correlation scheme can be expanded easily to any number of input signals. Since digital values can be stored indefinitely, multiple excitation beams and wide beam separations can be accommodated. The data on the bus can be organized in a convenient format, so that it can be interpreted directly by modules that have access to the bus. The bus signals can, for example, be used for complex multiparameter sort decisions or for the generation of histograms in real time. However, the correlation of asynchronously digitized values can present problems. If the storage and retrieval of data get out of step, correlation errors occur. Unlike correlation errors in analog electronics, mismatches in digital data can be carried over to subsequent events. High speed digital circuits may be susceptible to strong electromagnetic fields. For instance, the switching on of a high power laser may cause a disturbance on the power supply that may trigger some of the timing circuits. Such a glitch in the timing logic, which would only cause a single erroneous measurement in analog electronics, may be propagated for many measurements if it causes misalignment of the data stacks in a digital system. In the digital correlation scheme according to the invention, the manner in which the system handles timing errors (which can be kept low, but can never be completely prevented) is designed to minimize timing errors and to prevent error propagation.

Maximizing the Throughout Rate of Parallel Input Channels

The speed of an acquisition system that is organized in parallel input channels is independent of the time separation between the excitation beams. The maximal throughput rate is solely determined by the cycle time of the individual input channels. The pulse digitization process can virtually eliminate the system dead time.

Figure 2B:
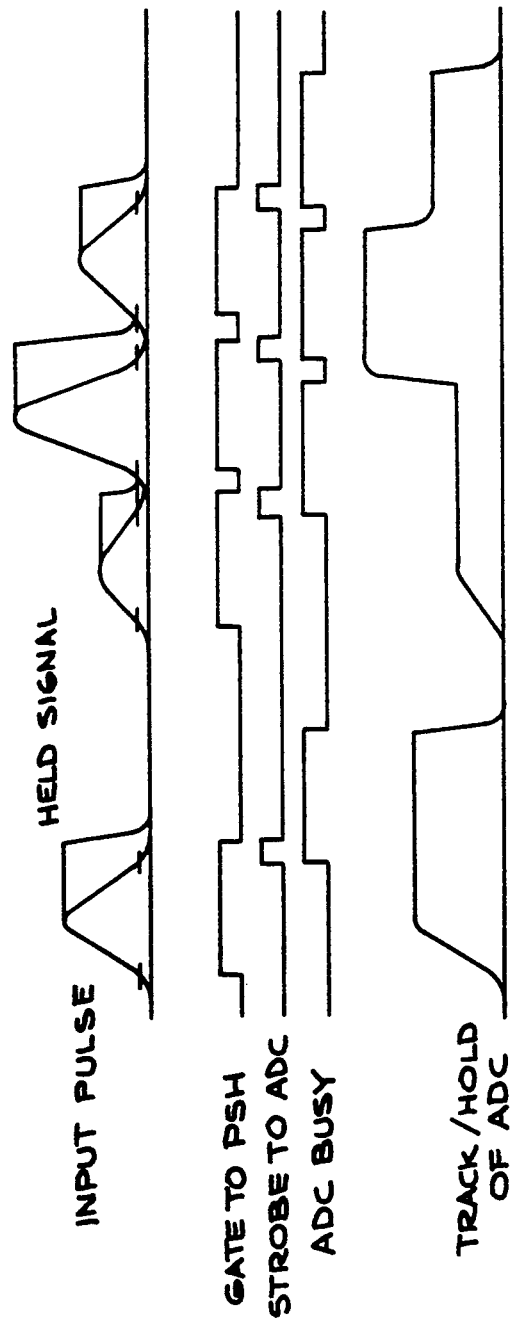
FIG. 2B shows the two-step pulse digitalization process of staggering the pulse sampling step and the AD conversion to shorten the cycle time of the pulse digitization process.

In the processing system of the invention, the pulse digitization has been divided into two steps that are carried out by separate circuits. An externally gated analog pulse sample/hold circuit (PSH) translates pulse size (the height, area or width of an input pulse) into a voltage (FIG. 2B). This voltage is accepted by a track/hold circuit at the input of an analog-to-digital converter (ADC). Since the activities of the two circuits need only to overlap during the short interval (strobe to ADC signal) in which the analog PSH output is transferred to the ADC module, the operation of the two circuits can be staggered in time. After the signal transfer, the PSH is free to accept the next event. While the ADC digitizes the signal (ADC busy), the analog processing circuit can measure the next pulse (gate to PSH). As long as the time interval between pulses that enter the analog circuit is longer than the maximal AD conversion time, the two activities remain correlated. By so staggering the pulse sampling step and the AD conversion, pulse processing cycle time is shortened.

Figure 3:
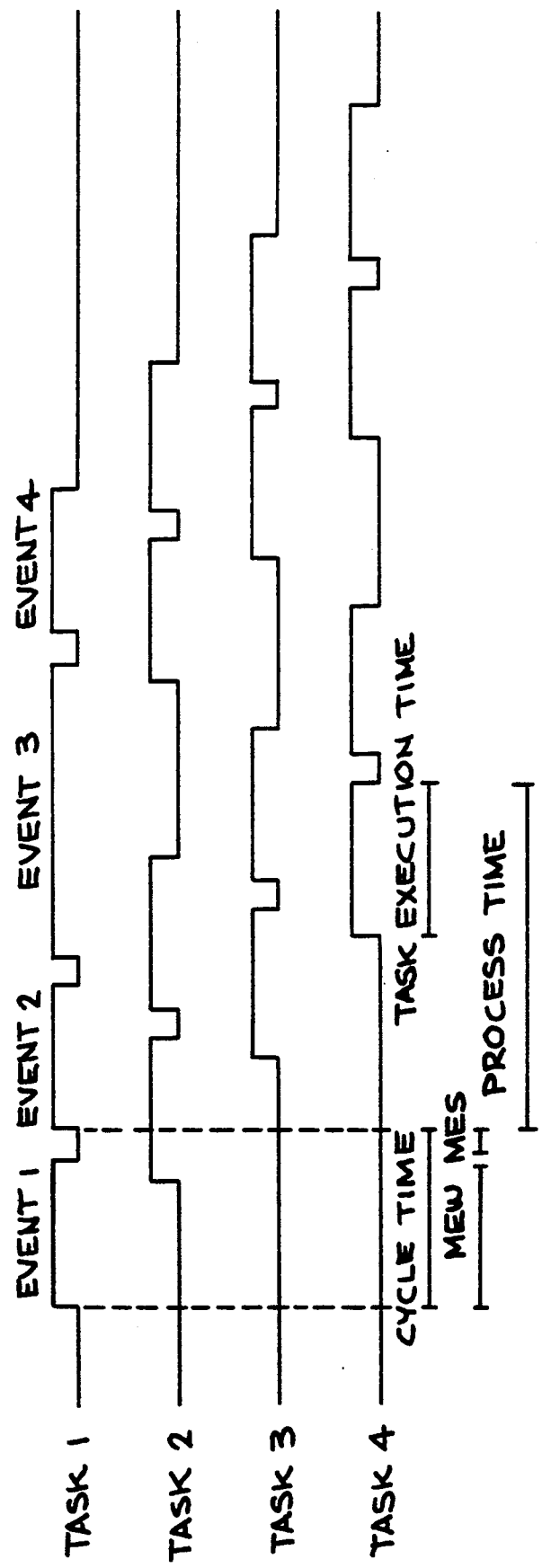
FIG. 3 shows a timing diagram for a process consisting of four staggered tasks.

Division of a process into tasks that can be executed in parallel greatly increases the throughput capacity of that process. FIG. 3 is a timing diagram of a process that consists of four staggered tasks (operations on a signal). In general, the maximum rate of events that a process of staggered tasks can accommodate is determined by the task with the longest execution time. If events enter the process at a higher frequency than the maximum throughput rate of the slowest task, pile-up will occur. When this happens, events may get lost or may get lumped together. Therefore, all tasks (except the first) in the process should be of equal duration. This time period is called the task execution time. The duration of the first task, which is called the event width, can be longer, but cannot be shorter than the task execution time. Thus, the minimal event width (MEW) should be equal to the task execution time. Furthermore, the events must be separated by a minimal time interval. This minimal event separation (MES) gives the input task time to switch from its processing mode to the pulse sampling mode. The MES also allows some inaccuracy in the timing of the subsequent process tasks. The shortest time interval between events that can enter a process of staggered tasks is the MEW plus the MES. This is the cycle time of the process.

The throughput capacity of an acquisition system is often specified by the system's dead time, which is defined as the time interval during which a new pulse might occur but cannot be accepted. FIGS. 4A, B illustrate how the event width and the cycle time are related to the dead time of a parallel processing acquisition system. FIG. 4A shows the timing of pulses that are shorter than the minimal event width, i.e., a system with a cycle time that is considerably longer than the pulse width. The dead time of the system is the cycle time minus the pulse width. The second pulse cannot be processed because it arrives within the cycle time of the system. If the pulse width is longer than the minimal event width, the dead time becomes equal to the minimal event separation (FIG. 4B). Such a system can be realized with electronics that measure the peak height of a pulse only. Since the peak height measurement is done in the first half of the pulse and the signal can be transferred to the ADC during the decay of the input pulse, the task execution time can be kept shorter than the pulse width.

The flow of data through p parallel input channels that merge into a common bus will proceed without pile-up if the cycle time of the bus is p times shorter than the cycle time of the individual input channels. Since the input channels of a flow cytometer receive pulses asynchronously and emptying of the digitized values onto the bus is a synchronous, cyclic process, the channel/bus interface must be provided with temporary storage buffers. No data is lost if the capacity of the channel buffers is greater than the maximum number of events that can be in transit at any given time. If the interval between the time that a particle crosses the first and the last excitation beam is $\Delta t$ and the digitization process consists of n tasks, then the minimum buffer capacity per input channel should be $n + \Delta t/\text{cycle time}$.

Flow cytometers usually operate with pulses in the range of 2-5 $\mu s$. Moderately priced, high resolution sample hold/ADC combinations that process pulses in this time domain are readily available. By combining such units into parallel input channels, pulse processing electronics with a dead time under 500 ns can be achieved. The dead time is then independent of the number of parallel input channels or the total channel processing time. This compares favorably to traditional methods of data acquisition in flow cytometry, which may result in dead times as long as 50–100 $\mu s$ (beam time separation).

Minimizing Correlation Errors

It is important to minimize the cycle time of a pulse processing system for reasons other than increasing the maximum throughput rate. Pulses that arrive during the dead time are not registered by the system as separate events and may, therefore, cause erroneous measurements. Two signals that occur in the same cycle period may be registered as a single event. For instance, the fluorescence of a bright particle that closely follows a dull cell may be mistakenly attributed to the dull cell. Such a sequence of events is not uncommon in immunofluorescence measurements. In the analysis of rare fluorescent events, pairing errors may be the major limitation in the number of positive events that can be detected above background level. To illustrate the potential significance of pairing errors, consider an acquisition system with a cycle time of 10 $\mu s$ analyzing events at a rate of $10^3/s$. Approximately 1% of the particles will pass the system within the cycle time of the previous pulse. Each case is a potential cause for a pairing error. If only 1% of such events result in an erroneous positive measurement, the false positive background is 1 in $10^4$. In real experiments, the throughput rate is often higher and the cycle time of the electronics is usually longer.

The probability of pairing errors decreases as the cycle time of an instrument is reduced and as its time resolution is improved. Lowest error rates occur when the interval during which the pulse is sampled (the aperture time) is much shorter than the pulse width. The minimum error rate is reached when the analog pulse sampling is bypassed altogether and peak sampling is done directly with the sample/hold circuits of the ADCs. In that case, only those particles that pass the illumination beam in perfect coincidence will cause correlation errors. Those events can never be separated on the basis of timing alone.

The correlation errors discussed above are due to coincident passage of particles through the illumination beam. They are dependent on sample density, flow rate, system aperture time and illumination spot size. A second class of correlation errors may arise due to mistakes of the acquisition instrument itself. Asynchronous pulse handling carries some risk of electronic correlation errors. Such errors tend to be propagated over several measurements. Digital electronics for pulse processing should be designed and tested carefully so that the advantages of parallel pulse processing are not negated by the introduction of digital errors.

Parallel Pulse Processing Instrumentation

The instrument can consist of up to 256 parallel acquisition channels (since 8 bits are used to identify the channel). The output of these channels are linked over a digital bus. The acquisition channels and control logic are located on circuit boards that slide into the bus. The configuration of the system can be modified by removing or adding acquisition modules. The system that will be described here consists of 8 pulse processing channels. Different pulse processors determine pulse width, pulse height or pulse area. The control electronics are set up to deal with three excitation beams. The cycle time of the system is 5 $\mu s$.

Figure 5A:
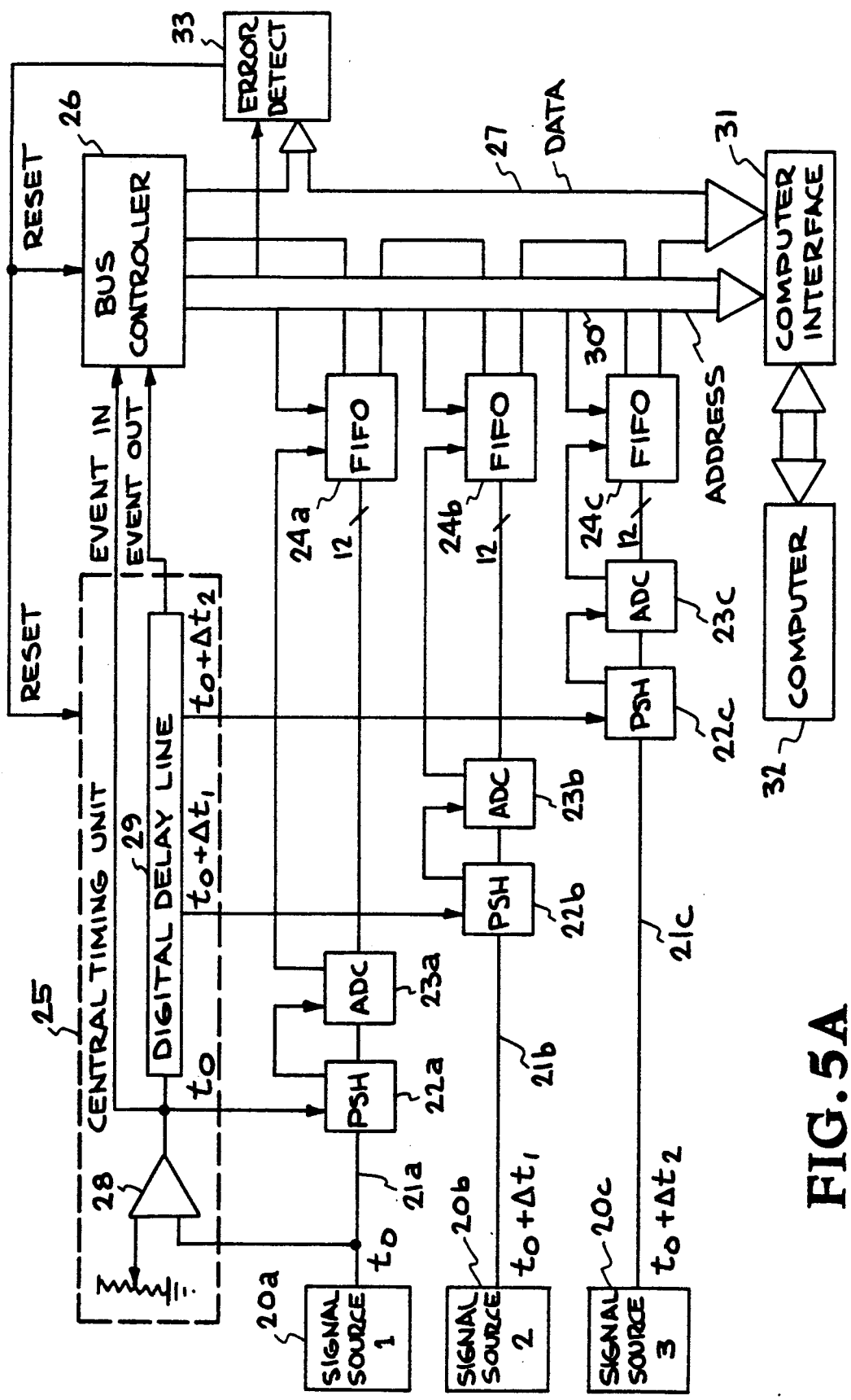
FIG. 5A is a schematic diagram of a parallel pulse processing system for a flow cytometer with multiple illumination beams and multiple detectors.

FIG. 5A is a shematic diagram of the parallel pulse processing circuitry for a flow cytometer with multiple (3) illumination beams. Light (fluorescence) from a particle is picked up by three sets of detectors 20$a,b,c$. An event that reaches the first detector 20$a$ at $t_o$ is registered by detectors 20$b$ and 20$c$ after a delay of $\Delta t_1$ and $\Delta t_2$ respectively. Each detector 20$a,b,c$ is connected to a respective parallel input channel 21$a,b,c$ which contains in series a respective pulse sample hold circuit (PSH) 22$a,b,c$ followed by an analog-to-digital converter (ADC) 23$a,b,c$ followed by a FIFO buffer 24$a,b,c$.

The activities of the system are directed by two controllers. The central timing unit (CTU) 25 sets up the timing sequence of the pulse digitization process. When the CTU has finished its task, it hands control over to the bus controller 26 which regulates the transport of data over the data bus 27. The CTU detects events on the first channel (21$a$) and triggers the analog pulse sampling modules (PSH) 22$a,b,c$ in the proper sequence. The CTU 25 delays the gate signals for the pulse sample hold circuits (PSH) 22$b,c$ such that the signal sampling coincides with the passing of the particle through the respective beam. The CTU 25 contains a trigger circuit 28 which receives a timing signal from the first channel 21$a$. The trigger circuit 28 of CTU 25 provides an undelayed timing signal $t_o$ to the first PSH 22$a$. The CTU 25 also contains a digital delay line 29 connected to the output of trigger circuit 28 to provide appropriate delayed timing signals to remaining PSH circuits 22$b,c$. The pulse samplers 22$a,b,c$ initiate the AD conversion by connected ADC's 23$a,b,c$. The results of the AD conversion are temporarily stored in FIFO buffers 24$a,b,c$ on the AD conversion boards. The outputs of all FIFO buffers 24$a,b,c$ are connected to a common (parallel) data bus 27. After all conversion steps have been completed (after a particle has passed all measurement beams), the bus controller 26 is activated. The bus controller 26 then sequentially addresses the ADC buffers 24$a,b,c$ over address bus 30. When addressed, each buffer shifts the value in the bottom register onto the data bus 27. The data on the data bus 27 are sent over a buffered interface 31 to a computer 32 that analyzes and/or stores the data. The data can also be read directly by real time modules. Examples of such real time functions are display monitors, sort look-up tables and event counters.

The System Trigger

The system trigger has four tasks: 1) it detects an event at the first excitation beam and starts the timing cycle of the pulse digitization process; 2) it assigns a sequence number to an event; 3) it prevents pulse pile-up by locking out events that occur within the cycle time of the instrument; and 4) it ensures that the trigger pulses are separated by a minimum time interval.

A threshold crossing by a signal from a particle that enters the first excitation beam generates a trigger pulse. This pulse activates the pulse sample/hold (PSH) circuits that accept signals from the first beam. This "event detected" pulse is also sent to digital delay lines that will generate the gate pulses for the PSH circuits of the subsequent excitation beams.

The system trigger regulates the spacing between the "event detected" pulses. It guarantees that the interval between two pulses is not shorter than the conversion time of the ADCs. After the main trigger has been activated, it is disabled for a set period (the minimal event width, MEW). Events that occur during this period are ignored and will not result in a trigger signal. The trigger circuit also ensures that there is a minimum time between the falling edge of a trigger and the rising edge of the next pulse (the minimal event separation, MES). The minimum pulse spacing prevents trigger pulses from merging in subsequent digital circuitry. The sum of MEW and MES is the cycle of the system (FIGS. 4A,B).

Figure 5B:
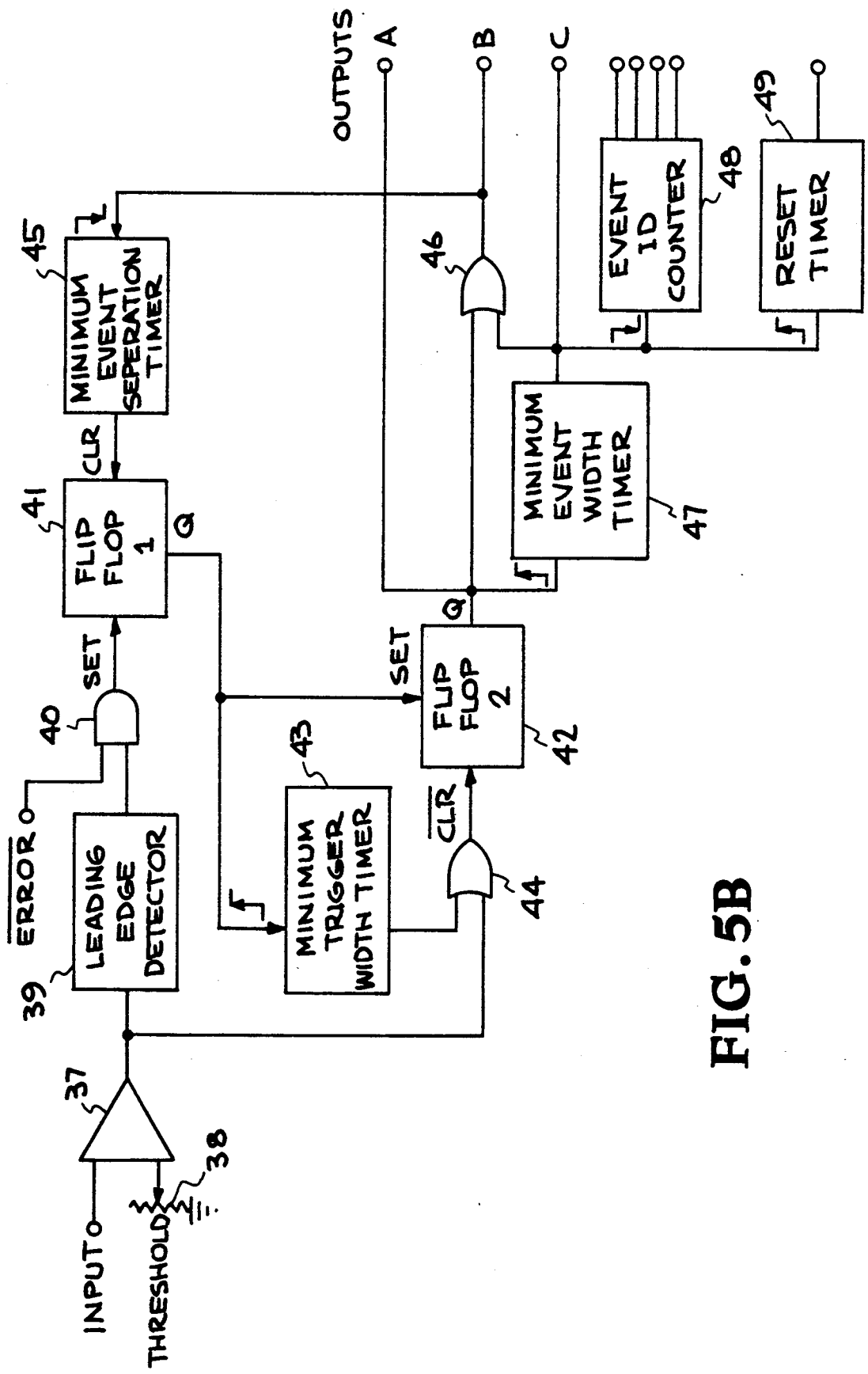
FIG. 5B is a schematic diagram of the trigger circuit.

A trigger unit that behaves as described is schematically shown in FIG. 5B. The output of a comparator 37 goes high when the input signal rises above an adjustable threshold, which is set by means of an input potentiometer 38. Upon a low to high transition of the comparator 37, a leading edge detector 39 connected to the output of comparator 37 generates a narrow pulse (50 ns). An input gate 40 (e.g., an AND gate) that may be controlled by error circuitry, is connected to the output of comparator 37 and can be used to block the incoming pulses. If the leading edge pulse passes the input gate 40, it sets a first flip/flop (FF1) 41. FF1, in turn, sets a second flip/flop (FF2) 42, and starts the minimum trigger width (MTW) timer 43. FF2 is cleared when both the comparator 37 output and the MTW timer 43 are low. The outputs of comparator 37 and MTW timer 43 are connected to the CLR input of FFL through OR gate 44. Thus, FF2 represents the true width of the accepted pulses with a minimum duration that is determined by the MTW timer 43. A low to high transition of the output of FF2 activates the minimum event separation (MES) timer 45 through OR gate 46. The MES timer 45 releases the FF1 for the next trigger cycle. A third timer, minimum event width (MEW) timer 47, is started when FF2 is set. The MEW timer takes over if FF2 is set shorter than the minimum event width time. The output of MEW timer 47 is also input into OR gate 46.

The trigger circuit has three trigger outputs: A, B, and C. Output A represents the true width of an accepted input pulse with a minimum duration set by the MTW timer 43. Output B represents the width of an accepted input pulse with a minimum duration set by the MEW timer 47. Output C represents a trigger signal of a constant duration (the minimum event width) for each accepted input pulse. All three meet the timing requirements and can be used to trigger subsequent delay lines or pulse processing circuits.

Figure 5C:
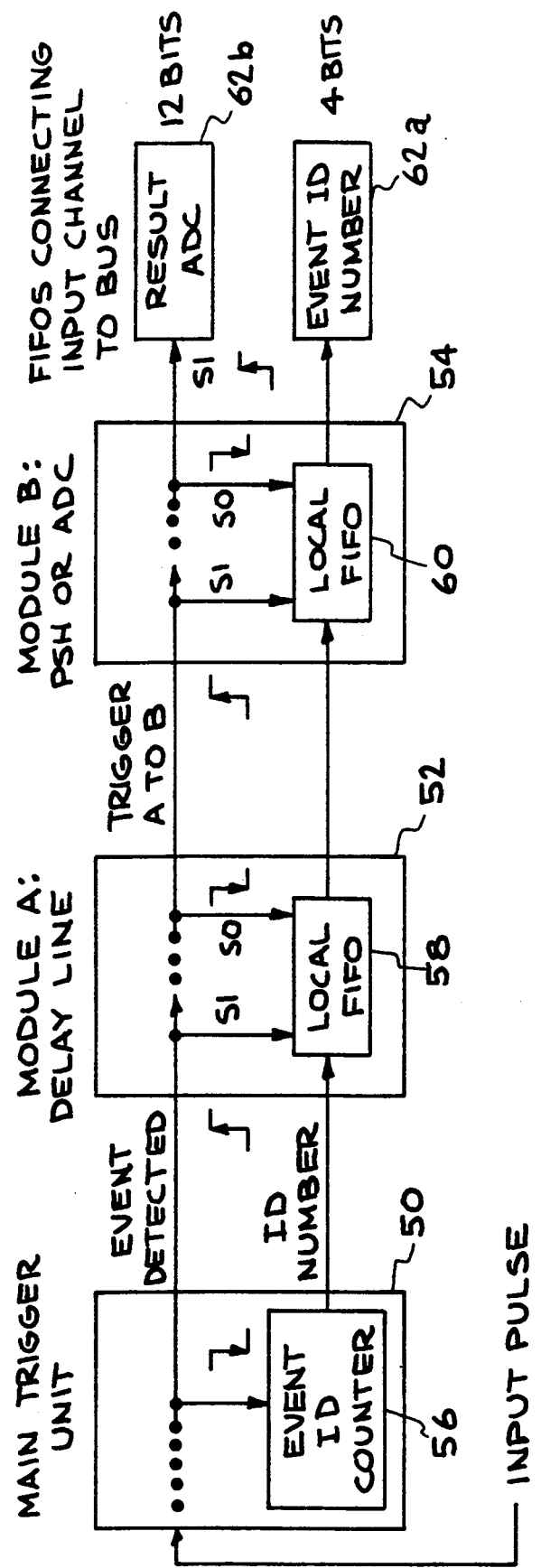
FIG. 5C is a schematic diagram of input channel circuitry for passing the event ID number between the modules of the input channel.

To allow a check of the synchronization of the pulse digitizing process, the trigger circuit assigns an ID number to each accepted event. The trailing edge of each trigger pulse will increment a 4 bits counter (event ID counter) 48. The counter value at the leading edge of the trigger pulse is the event ID number. This ID number is handed to all subsequent modules. The process goes as follows for two modules in the pulse digitization process (FIG. 5C). Module A (for instance a digital delay line) 52 is activated by the main trigger unit 50. After completion of its task, module A activates module B (for instance a pulse Sample Hold circuit) 54. At the leading edge of the trigger signal, A will read the value from the ID counter 56 and shift it into a local FIFO 58. When A triggers B, B takes the value in the bottom stack of A's FIFO 58 and shifts it into its own local FIFO 60. At the trailing edge of the trigger signal from A to B, the bottom value in A's FIFO 58 is discarded and all values in the local FIFO 58 stacks are shifted to the next position. This process is repeated as the event is handed from module to module. In the final step, the event ID number will be shifted into a 4 bit FIFO 62a that connects the ADCs with the digital data bus. The FIFO 62a now contains the event ID number (4 bits) and a parallel 12 bit FIFO 62b contains the value of the AD conversion (12 bits). If this process proceeds correctly, values that belong to the same event should have identical ID numbers, since they are all initiated by the same main trigger pulse. An error detection unit 33, connected to the data bus 27, checks the ID number (as shown in FIG. 5A). When a synchronization error is detected, a reset (error) signal is generated and all data in the parallel input channels are discarded. The error signal will also temporarily block the main trigger unit so that all digital delay lines can be emptied.

The leading edge of each accepted pulse also triggers the reset timer 49 (FIG. 5B). The reset timer 49 is a retriggerable timer. When activated, its output goes high for a time interval that is longer than the total event processing time. Thus, a low output of the reset timer indicates that no events are being processed. The output of the reset timer controls the same reset line that is activated by the error detection circuit. This provides an automatic synchronization of the input channels upon start-up and when no events are being processed.

Figures 9, 10:
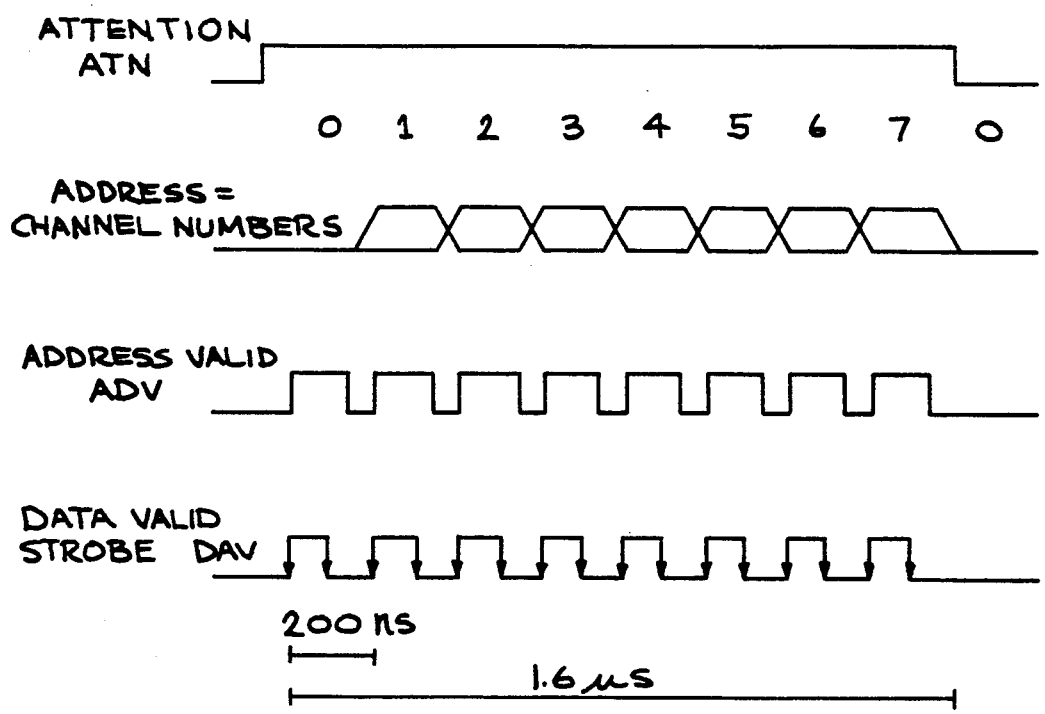
FIG. 9 is a timing diagram of the bus controller output.
FIG. 10 is a diagram of the bus status (data package) at consecutive DATA Valid strobe signals.

The parameter values that belong to the same event form a data package. The data packages are transferred over the bus to the various modules and to the acquisition computer. At the beginning of a package transfer, the attention line (ATN) (as shown in FIG. 9) of the bus goes high. When the transfer is complete, the ATN line goes low. The data are valid upon a high low transition of the data valid (DAV) line. FIG. 10 represents the status of the data bus (a data package) at consecutive DAV strobe signals. The 24 bus bits contain the following information. Eight bits identify the input channel whose value is being put onto the bus. The channel number is put on the bus by the bus controller. Since 8 bits are used, 256 channels or detectors can be included. Twelve data bits represent the measured value itself. Four bits represent the event ID number. These last two values (16 bits) are found in the bottom stack of the FIFO of the input channel that corresponds with the channel number. The integrity of a data package can be tested in several ways. All input channels should be represented once in the package. If one of the channel numbers is missing, or if one of the numbers is present more than once, a bus transfer error has taken place. In addition, all event ID bits should have the same value. If different ID numbers are found in the same package, a trigger error has occurred in one of the input channels. A special module on the bus (the error detection circuit) checks the identity of the event ID numbers. If the ID numbers are not identical, the circuit generates a reset signal.

Figure 6:
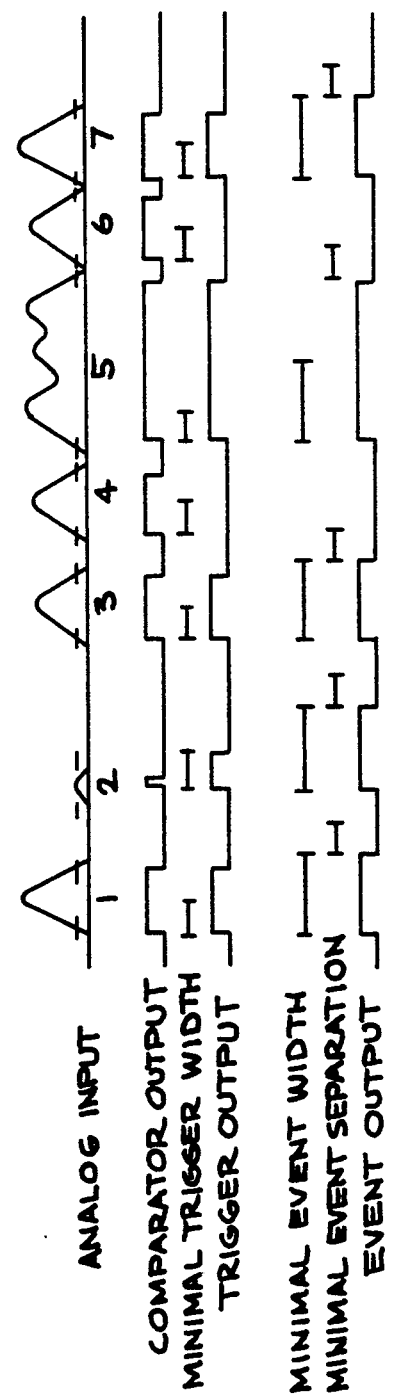
FIG. 6 is a timing diagram of the system trigger.

An illustrative timing sequence of the system trigger is depicted in FIG. 6. The cycle time is set at 5 $\mu$s. The minimum event separation is 0.5 $\mu$s. The trigger output pulse has the length of the comparator output with a minimum of 1 $\mu$s (minimal trigger width). The propagation delay (the time between a threshold crossing and the appearance of the trigger pulse on the output of the circuit) is 70 ns. The pulses and timing segments of FIG. 6 show how the trigger circuit responds to a complex input signal. Only those Pulses that start after the cycle time of the previous pulse and/or are separated by more than the minimal event separation result in a trigger output signal. Pulse 4 does not result in a system trigger because it recurs within the cycle time of its predecessor. Pulse 5 is longer than the minimal event width. Therefore, the timer that determines the minimal event separation is started at the end of the pulse rather than at the end of the task execution time. Pulse 6 is ignored because if follows the preceding event too closely. Pulses that are shorter than the minimal trigger width (pulse 2) are elongated to meet the trigger pulse characteristics.

Digital Delay Line

The pulses from the system trigger 28 are delayed by the digital delay line modules 29 (FIG. 5A). The output of these modules serve as gate pulses for the electronics (PSH's 22b,c) that process the signals from the subsequent excitation beams. The delay is achieved using an SRAM (static random access memory) as a shift register. A clocked counter cycles through all addresses of the SRAM at a frequency of 10 Mhz. Thus, a new memory location is addressed every 100 ns. In that interval, the content of that location is put on the output of the delay module. The memory content is then replaced by the input state of the circuit. Variable delays are obtained by varying the length of the counting cycle. This circuit will delay input pulses with a jitter of 100 ns. Since the system trigger guarantees an event separation of 500 ns, the jitter cannot cause the merging of events. The delay lines can operate in two modes. The delayed pulse can have the same width as the input pulse. Alternatively, the delayed pulse can be given a constant width Since the delayed pulses serve as gate pulses for the PSH circuits, the fixed width output pulse should not be longer than the minimal event width.

End of Conversion Pulse

The end of conversion pulse serves as a signal (event out) to the bus controller that an event has passed all measurement beams and has been digitized. The signal is generated by a digital delay line set at a constant delay time. The time is chosen slightly longer than the maximum pulse separation plus the conversion time. After this signal, the bus controller starts the cycle that transfers the digitized pulse information to the bus.

Pulse Sample/Hold

The signals from each detector of the flow system are amplified and given to a pulse sample hold circuit. These circuits receive gate pulses from the system trigger or from the delay lines. When the gate is not active, the outputs of the PSH circuits follow the input signals. When the gate is active, the circuits sample their input. A PSH circuit can be configured in two ways. In one mode, it integrates the input signal during the gate interval. In the other mode, it holds the peak value during the gate. The held value is passed on to the ADC circuits. A timing diagram of the PSH circuit is shown in FIG. 7. The PSH circuit samples the input during the gate pulse. The PSH gives a strobe pulse to the track/hold input of an ADC circuit after the task execution time (4.5 $\mu$s). If the gate signal is longer than the task execution time, the strobe pulse will be generated immediately at the end of the gate period. The strobe pulse should be shorter than the minimal event separation. The analog input of the PSH circuit is disconnected (connected to ground) during the period between the end of the gate pulse and the ADC strobe pulse. Thus, events that occur within the cycle time but after the gate period do not influence the measurement.

Figure 8A:
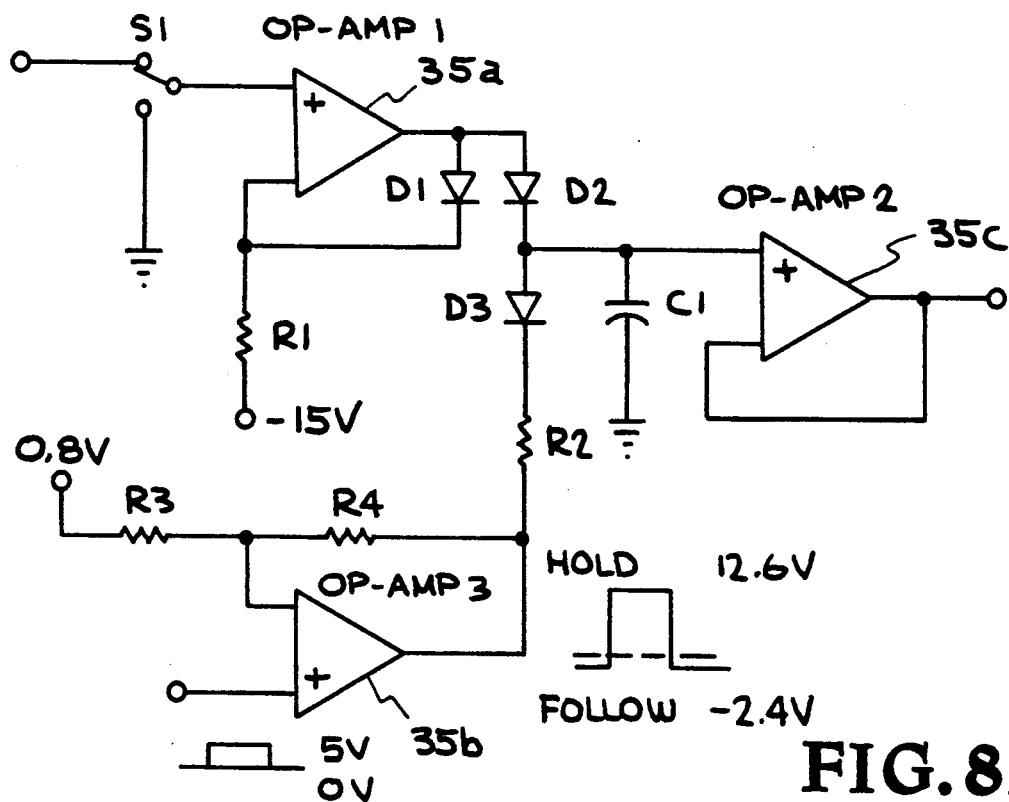
FIGS. 8A, B are schematic diagrams of the analog part of the pulse sample hold circuit, in a peak hold configuration and as a pulse integrator, respectively.
Figure 8B:
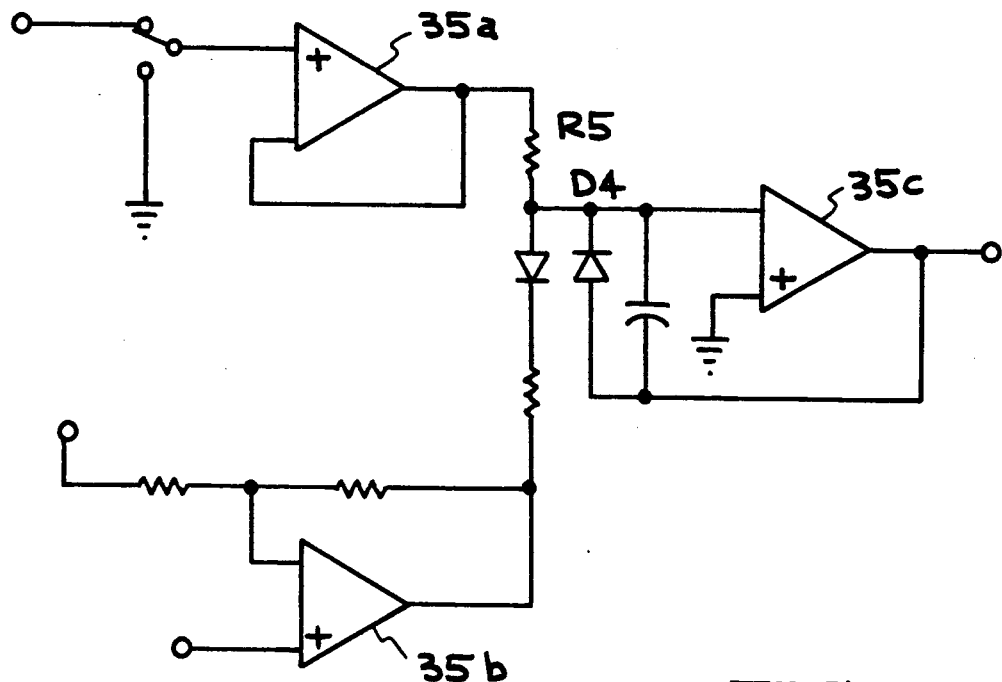

A schematic of the PSH circuit is shown in FIGS. 8A, B. FIG. 8A shows the peak hold configuration. FIG. 8B shows how this circuit can be modified into a pulse integrator. The circuit shown is capable of determining the peak height (FIG. 8A) or area (FIG. 8B) of fast pulses (1-2 $\mu$s) without switching transients on the output. The PSH circuit of FIG. 8A is made up of three operational amplifiers 35a,b,c. The input signal is connected to the positive input of op-amp 35a through switch S1. The outputs of op-amps 35a,b are connected to the positive input of op-amp 35c through diode D2 and diode D3/resistor R2, respectively. The PSH circuit is switched between the follow and hold mode by changing the output voltage of op-amp 35b. When its output is below ground the voltage over C1 and thus the output of op-amp 35b will follow the input signal. The circuit is compensated for the voltage drop over the hold diode (D2) by placing an identical diode (D1) in the feed back loop of the preceding amplifier 35a. The two diodes are in thermal contact and provide thermal stability to the circuit. During the gate period, the output of op-amp 35b is switched to >10 V and the voltage over C1 will hold the peak value of the input signal. Switch S1 disables the input in the interval between the end of the gate pulse and the pulse sample hold cycle. As shown in FIG. 8B, the PSH circuit is modified to function as a pulse integrator by omitting D1 and R1, replacing D2 with R5, and placing C1 in the feedback loop of op-amp 35c, which now uses the negative input as the input/feedback terminal. The integrated signal that is held over C1 is discharged through a parallel diode D4 when the output of op-amp 35c goes negative.

The Bus Controller

After a particle has traversed all excitation beams and its pulse values have been determined and digitized by the ADCs, the measured values are temporarily stored in buffers on the ADC boards. The buffers are of the first-in-first-out (FIFO) type. They can be visualized as containing a stack of values. The oldest values are at the bottom. Newly arriving values are added to the top. When a particle has been processed by all stations, the bottom values in the stacks represent measurements of that particle. These values are sent over the bus to the computer and to other modules that require the pulse parameters.

The bus controller 26 directs the transfer of data from the FIFOs 24a,b,c over the bus 27 (FIG. 5A). It receives an "end of conversion" ("event out") signal from the central timing unit, indicating that an event has been processed. The controller then addresses the individual output buffers of the ADC boards in sequence. Three control lines indicate when a data transfer is in progress and when the address and/or data lines contain valid information. When an ADC sees its address in combination with an "address valid" (ADV) signal, it responds by putting the bottom value in its data stack on the bus. At the end of the "address valid" pulse, the bottom stack is cleared and the values in the FIFO are shifted down one position. A timing diagram of the control and address lines is shown in FIG. 9. The emptying of one buffer takes 200 ns. Thus, the total bus cycle for 8 pulse parameters is 1.6 $\mu$s.

As long as the bus cycle is shorter than the cycle time of the system, the buffers are emptied faster than they are filled. The FIFOs do not contain more values than the number of events in transit between the illumination beams. There is a fixed interval between the time a particle enters the first laser beam and the time digitized values appear on the bus. This makes it possible to use the values on the bus for sort decisions. Since the data package contains all the information needed for sorting, "look-up table" sorting is easily implemented.

The bus controller also regulates the status of a central reset line on the bus. The reset line clears all the FIFO buffers. When there are no events being processed by the system, the reset line is activated. As soon as an event is registered by the central timing unit ("event in" signal to bus controller), the reset line becomes inactive. The FIFOs are then ready to accept data. The reset line is again activated after the event has passed all laser beams ("event out" signal to bus controller) and its parameters have been sent over the bus. If a new event has occurred in the meantime, the reset pulse is suppressed. This scheme guarantees that the system is in a known state when it is idle and that possible synchronization errors of the FIFOs are automatically corrected.

The Error Detection Circuit

The prevention and detection of correlation errors takes place at three levels. By having a central unit, the system trigger, control the timing of all other modules and by adhering to a precise timing scheme (minimal pulse width and the minimal pulse spacing matched to the cycle time of the input channels), the incidence of correlation errors is greatly reduced. Nevertheless, occasional correlation errors will take place. The automatic reset function of the bus controller prevents these errors from being propagated. At the third level, a circuit 33 that actively detects correlation errors is used. This circuit 33 resets both the central timing unit 25 and the bus controller 26 as soon as a pairing error is detected. The number of detected errors can be monitored. This serves as a quality check for proper operation of the instrument. A poor cable connection or a malfunctioning module will generate large numbers of pairing errors and can be easily located. Under normal circumstances, the system should generate only a few correlation errors per day.

The error detection circuit uses the ID number that the system trigger assigns to each event. This number is handed to the digital delay lines, the PSH circuits and the ADCs. It is finally stored with the data in the ADC FIFOs. If the instrument operates properly, all values at the bottom of the FIFO stacks should have the same ID number. The error detection circuit checks if all ID numbers of the parameters that belong to the same event are identical. When the first parameter (address 0) appears on the bus, the error detection module reads the event ID number. It compares this number with the ID numbers that are put on the bus with the next 6 pulse parameters. When the bus controller asks for parameter 7, the error detection circuit puts a logic 1 on the bus if all ID numbers were the same and a 0 if one or more of the numbers deviated from the first ID number. Since this "error detected" signal is part of parameter 7, the occurrence of an error is communicated to all modules that read data from the bus. The "error detected signal" is seen by the computer and the sort electronics. Thus, erroneous measurements due to correlation errors can be excluded from event analysis and will not result in sort impurities.

When the error detection circuit spots an error, it will also activate the reset line. The function of this line is described in the "System Trigger" section.

The ADC Boards

The ADC boards link the analog and digital domains of the system. They receive asynchronous analog signals from the PSH circuits. They export the digitized values in an orderly, synchronized manner over the digital bus. The ADC modules contain a track/hold input, an AD converter and a FIFO buffer. Each ADC has a unique address. The control and address lines of the bus select the boards and initiate the transfer of data.

At the input of the circuit is a monolithic track/hold (TH) circuit with an aperture time of 20 ns and a settling time of 500 ns (Harris, HA 5330-5). A low-to-high transition on the strobe input latches the TH voltage and starts the AD conversion cycle. For fast pulses or for measurements that require a narrow time window, the TH input can be tied directly to the output of a signal amplifier. If the pulse parameter of interest requires a longer measuring window, such as peak height during an interval or pulse integral, a PSH circuit is connected between the signal amplifier and the ADC board. The ADCs are 12-bit successive approximation ADCs (Analog Devices, AD 578LN). The FIFOs used are 74HCT 40105 (Signetics). Three such FIFOs are configured as a buffer, 16 words deep and 12 bits wide. Their access time is 30 ns.

Other Pulse Parameter Units

There are pulse properties other than peak height or area that can be represented in digital format. Suitable modules can be used in place of the ADC modules. These modules interact with the trigger signals and the bus in a manner similar to that of the ADCs. For example, the pulse width can be digitized directly by counting clock pulses while the pulse is above a threshold. The rising edge starts a clocked counter. The falling edge stops the counter and shifts its value into a FIFO buffer. The same procedure can be used to measure intervals between pulses. These measurements can be used to detect doublets, or pulses that are too closely spaced.

Another example of a measurement that is already available in a digital format is the time at which the event occurred. A digital clock can be directly attached to an input channel.

The Bus Monitor

The digitized pulse values appear on the bus as an organized package. For each event there are 8 sets of data each containing a channel number, an event ID number, and 12 bits that are the result of the AD conversion. The complete package passes onto the bus in 1.6 $\mu$s. Specialized modules can read these data and perform specific operations in real time. The simplest operation is the display of a dot plot. A module takes the values of two parameters of a data set from the bus and feeds them to two digital-to-analog converters (DAC). The DACs are attached to the x and y inputs of an oscilloscope. A more complex variant stores the data first in two 4 kbyte memories: one for the x parameter and one for the y parameter. Incoming new data are written at the memory locations that contain the oldest information. Two DACs continuously display the contents of the memories on an oscilloscope, thus presenting a quasi-stationary dot plot of the 4096 most recent events. A front panel control determines which pair from the 8 pulse parameters is to be displayed.

Computer Interface

The computer interface reads the data as they appear on the bus and sends them to the computer. To compensate for the asynchronicity of the bus and the computer transfer process, the data are buffered in a large FIFO buffer (Integrated Device Technology, IDT 7204, 50 ns access time). Two of these FIFOs are configured as a buffer, 4096 words deep and 16 bits wide. The buffer is activated and reset by software control. The "half full" flag of the buffers is used to prevent overflow. The circuit that shifts data into the buffer has been wired so that only complete data sets are stored. If a read instruction is received while a bus transfer is in progress, the interface will wait until the cycle is completed before it starts taking data from the bus. In the present setup, the interface is connected to a Hewlett Packard 9000 series computer (model 330) via a GPIO interface (HP 98622A). The data transfer protocol sustains an effective DMA transfer of 2 Mbyte/s.

The interface can also be used to send instructions to the modules on the data bus. The bus lines that carry data to the modules (16 data and 7 control lines) are separate from the bus lines that transfer data to the computer. In write mode, the computer interface serves as the bus controller and can direct data and instructions to individual or groups of modules. Several computers can be linked to the bus of the acquisition system. Thus, it is possible to use several dedicated computers in parallel: one for data storage, one for on-line data analysis, one for sorting control, etc. At any given time, only one computer can serve as the controller for write operations. The interface does not adhere to a manufacturer-specific bus protocol and can be easily adapted to any computer.

Results

Several data acquisition units with parallel signal inputs have been used on 2- and 3-laser analyzers and sorters. The latest version incorporates look-up table sorting directly from signals on the digital bus. Although the design aims at high system performance, the modules are built with standard electronic components. The average cost of the parts for most of the modules is approximately $200. This includes the manufacturing of specially designed, printed circuit boards. The ADC modules are approximately twice as expensive.

Despite their modest cost, these systems have been found to perform very well. The modular design has proven useful in a variety of experiments. Standard multiparameter immunofluorescence measurements, kinetic measurements, high resolution chromosome measurements, rare event analysis, fluorescence in situ hybridization, photo-damage cell selection and the analysis of algae populations are some examples of studies in which these instruments have been used. A high throughput rate is achieved while maintaining a low error rate. To determine the error frequency, the CTU is offered $2 \times 10^6$ random events/s. At that rate, the frequency of the pulses that are processed by the system are close to the maximum analysis and sort rate of $2 \times 10^5$ events/s. In a typical test, no correlation errors occur during a few hours of observation. Thus, machine-induced correlation errors are well below 1 in $10^8$ processed events. This is several orders of magnitude below the expected pairing errors of particles with perfect coincidence. The machines have been found to perform reliably. The electronics are rugged and insensitive to external analog or digital noise.

The acquisition system of the invention meets many of the requirements for high performance flow cytometry. The system can be optimized for a high throughput rate, high sort purity, high measurement fidelity or an acceptable compromise between these sometimes conflicting requirements. The user has extensive control over the timing of the pulse conversion process. A scheme of staggered pulse conditioning and AD conversion allows multiple excitation beam processing with a very short dead time. The timing and length of gate pulses for the pulse conditioners can be individually chosen. For conversion schemes that require narrow time apertures, the pulse conditioners can be bypassed and the ADCs can operate in a sample/hold mode. For rare event measurements, each channel can be provided with a circuit that excludes coincident or closely spaced pulses from analysis.

Parallel pulse processing allows a high event rate, but carries the risk of the accumulation of correlation errors. The invention makes the instrument as immune to electronic errors as possible. Irregular system triggering is prevented by the design of the system threshold. The timing electronics lock out closely spaced pulses and guarantee a minimum pulse spacing. Error propagation is prevented by automatic system resets when the system is idle. Furthermore, the system contains diagnostic circuits that check for electronic errors and reset the acquisition channels when an error has been detected. Together, these measures result in a system that can process asynchronously arriving pulses at very high rates with very low correlation errors.

The system is assembled from functional modules that can be replaced or recombined into different configurations. Configurations ranging from a simple one-laser, one-parameter analyzer to sorters that use many lasers and detectors to perform complex kinetic measurements can be assembled from the same modules. Other functions can be accommodated without design modifications, including pulse shape digitization, pulse shape sorting and dynamic sort windows that ar continuously adjusted on the basis of real time computer analyses.

Changes and modifications in the specifically described embodiments can be carried out without departing from the scope of the invention which is intended to be limited only by the scope of the appended claims.

We claim:

1. Apparatus for pulse processing and data acquisition from a plurality of detectors generating asynchronous event pulses from a single event, comprising:
   a plurality of parallel input channels, each of which receives one of the event pulses from a respective detector;
   pulse digitization means in each channel for digitizing the event pulse received in the channel;
   a channel FIFO buffer in each channel connected to the respective pulse digitization means;
   a common data bus connected to all the FIFO buffers;
   central control means external to the channels connected to each channel for providing a synchronizing timing signal to the respective pulse digitization means in each channel in response to a start signal from at least one of the channels to synchronize pulse digitization in each channel with detection of the event by the respective detector and to digitize each pulse on each channel substantially immediately after the pulse is input on the channel;

a bus controller connected to the data bus and to the control means for transferring correlated data from the FIFO buffers to the data bus following an actuation signal from the control means, the transferred data being correlated to the event.

2. The apparatus of claim 1 wherein the pulse digitization means in each channel comprises:

a pulse sample/hold module;

an analog-to-digital converter (ADC) connected to the pulse sample/hold module and having a track/hold input section;

wherein the pulse sample/hold module and ADC are operated in a staggered timing relationship by triggering the pulse sample/hold module on a gate pulse and triggering the track/hold input section of the ADC substantially immediately following the gate pulse to the pulse/sample hold module.

3. The apparatus of claim 2 wherein the control means further comprises an event ID number generation means for providing an event ID number for each event stored in the FIFO buffers.

4. The apparatus of claim 3 wherein the pulse sample/hold modules and analog-to-digital converters each further comprise a local FIFO buffer to transfer the event ID number from the control means to the channel FIFO buffer.

5. The apparatus of claim 1 wherein the control means further comprises:

minimum event separation generation means;
minimum event width generation means.

6. The apparatus of claim 5 wherein the control means further comprises minimum trigger width generation means.

7. The apparatus of claim 1 wherein the control means further comprises an event ID number generation means for providing an event ID number for each event stored in the FIFO buffers.

8. The apparatus of claim 7 further comprising error detection means connected to the data bus for detecting the event ID numbers in the FIFO buffers.

9. The apparatus of claim 1 wherein the control means further comprises a reset timer.

10. The apparatus of claim 1 wherein the control means further comprises blocking means for disabling the control means when a data correlation error signal is received by the blocking means and until a restart signal is received.

11. The apparatus of claim 1 wherein the control means comprises:

a comparator having its input connected to a start signal from the channels;

a leading edge detector having its input connected to the output of the comparator;

an input gate having an input connected to the output of the leading edge detector and another input connected to a blocking signal;

a first flip/flop having its set input connected to the output of the input gate;

a second flip/flop having its set input connected to the output of the first flip/flop and its clear input connected to the output of the comparator;

a minimum event separation timer connected to the clear input of the first flip/flop;

a minimum event width timer having an input connected to the output of the second flip/flop;

an OR gate having a first input connected to the output of the second flip/flop and a second input connected to the output of the minimum event timer and its output connected to the input of the minimum event separation timer.

12. The apparatus of claim 11 further comprising:

a minimum trigger width timer connected to the output of the first flip/flop;

an OR gate having an input connected to the comparator and a second input to the output of the minimum trigger width timer and its output to the clear input of the second flip/flop.

13. The apparatus of claim 1 further comprising error detection means connected to the data bus for detecting correlation errors in data transferred from the FIFO buffers to the data bus.

14. The apparatus of claim 13 wherein the error detection means further comprises a reset means connected to the control means and bus controller.

15. The apparatus of claim 1 wherein the FIFO buffer comprises a first buffer for storing the event ID number and a second buffer in parallel with the first buffer for storing digitization event data.

16. The apparatus of claim 1 wherein the control means further comprises:

trigger signal generation means;

a digital delay line connected to the trigger signal generation means for providing measured time delays to gating signals to the channels.

17. The apparatus of claim 1 further comprising an address bus connected from the bus controller to each FIFO buffer.

18. A method for pulse processing and data acquisition from a plurality of asynchronous pulses generated by a single event from a plurality of detectors comprising:

inputting an event pulse onto each of a plurality of parallel input channels;

digitizing each event pulse on each channel substantially immediately after inputting the pulse on the channel and synchronously with detection of the event by an associated detector;

storing the digitized event in a FIFO buffer on each channel;

transferring correlated stored digitized event data about a single event from all the FIFO buffers onto a common data bus.

19. The method of claim 18 further comprising generating an event ID number for each event pulse and storing the event ID number in the FIFO buffer.

20. The method of claim 19 further comprising comparing all event ID numbers from a single event on the data bus.

21. The method of claim 18 further comprising checking that a single event data entry is transferred to the data bus from every channel.

22. The method of claim 18 further comprising generating a minimum event separation and a minimum event width.

23. The method of claim 22 further comprising generating a minimum trigger width.

24. The method of claim 18 further comprising digitizing successive event pulses on each channel by initiating pulse sample and holding of a succeeding pulse while performing analog-to-digital conversion of a preceding pulse when the succeeding pulse occurs prior to completion of analog-to-digital conversion of the preceding pulse.

25. Apparatus for generating a trigger pulse, comprising:
- a comparator having its input connected to a start signal;
- a leading edge detector having its input connected to the output of the comparator;
- an input gate having an input connected to the output of the leading edge detector and another input connected to a block signal;
- a first flip-flop having its set input connected to the output of the input gate;
- a second flip-flop having its set input connected to the output of the first flip/flop and is clear input connected to the output of the comparator;
- a minimum event separation timer connected to the clear input of the first flip/flop;
- a minimum event width timer having an input connected to the output of the second flip/flop;
- an OR gate having a first input connected to the output of the second flip/flop and a second input connected to the output of the minimum event timer and its output connected to the input of the minimum event separation timer;
- wherein the outputs of the second flip/flop, the OR gate, and the minimum event width timer can be used as trigger pulses.

* * * * *